(12) United States Patent
Nikitina et al.

(10) Patent No.: US 8,337,734 B2
(45) Date of Patent: Dec. 25, 2012

(54) NON-STICK MEDICAL TUBING

(75) Inventors: Ludmila Victoria Nikitina, Raleigh, NC (US); Kenneth Whitley, Youngsville, NC (US)

(73) Assignee: CareFusion 303, Inc., San Diego, CA (US)

(*) Notice: Subject to any disclaimer, the term of this patent is extended or adjusted under 35 U.S.C. 154(b) by 60 days.

(21) Appl. No.: 12/880,036

(22) Filed: Sep. 10, 2010

(65) Prior Publication Data

US 2012/0064267 A1 Mar. 15, 2012

(51) Int. Cl.
 *B29C 47/88* (2006.01)
 *B29C 47/00* (2006.01)
 *D01D 5/24* (2006.01)

(52) U.S. Cl. ......... 264/211.2; 264/171.26; 264/171.28; 264/209.1; 264/209.7; 264/210.5; 264/210.6; 264/211; 264/211.12; 264/234; 264/345; 428/36.92

(58) Field of Classification Search .................. None
See application file for complete search history.

(56) References Cited

U.S. PATENT DOCUMENTS

| | | | | |
|---|---|---|---|---|
| 3,645,822 A * | 2/1972 | Widiger et al. | | 156/243 |
| 3,821,179 A * | 6/1974 | Powell | | 524/229 |
| 4,198,983 A * | 4/1980 | Becker et al. | | 604/266 |
| 4,495,312 A * | 1/1985 | Hata et al. | | 523/105 |
| 4,510,281 A * | 4/1985 | Smith | | 524/229 |
| 4,707,389 A * | 11/1987 | Ward | | 428/36.6 |
| 4,722,816 A * | 2/1988 | Ueno et al. | | 264/483 |
| 4,751,262 A * | 6/1988 | McKinney et al. | | 524/231 |
| 5,399,401 A * | 3/1995 | Powell | | 428/36.9 |
| 5,533,992 A | 7/1996 | Patel et al. | | |
| 5,614,297 A * | 3/1997 | Velazquez | | 428/212 |
| 5,932,307 A * | 8/1999 | Ryan et al. | | 428/36.9 |
| 6,497,965 B1 * | 12/2002 | Longmoore et al. | | 428/515 |
| 6,576,310 B2 * | 6/2003 | Shimada | | 428/36.9 |
| 6,673,053 B2 | 1/2004 | Wang et al. | | |
| 7,125,921 B2 * | 10/2006 | Yuan et al. | | 524/230 |
| 7,329,445 B2 * | 2/2008 | Ling et al. | | 428/36.91 |
| 7,491,889 B2 * | 2/2009 | Dinkelmeyer et al. | | 174/120 R |
| 2002/0104544 A1 * | 8/2002 | Ogushi et al. | | 128/207.14 |
| 2003/0175499 A1 * | 9/2003 | Phillips | | 428/323 |
| 2005/0277910 A1 * | 12/2005 | Dolla et al. | | 604/529 |
| 2006/0065427 A1 * | 3/2006 | Kummer et al. | | 174/110 R |
| 2006/0068182 A1 | 3/2006 | Wilhoit et al. | | |

(Continued)

FOREIGN PATENT DOCUMENTS

EP 1123715 8/2001

OTHER PUBLICATIONS

ISA/KR, International Search Report and Written Opinion for International Application No. PCT/US2011/050736, 9 pages, Apr. 18, 2012.

*Primary Examiner* — Jeffrey Wollschlager

(57) ABSTRACT

A method for manufacturing a non stick medical tube is provided. The method includes providing a first plastic resin to a tubing extrusion device and providing a second plastic resin to a tubing extrusion device, the second plastic resin comprising a medical grade amide compound. The method further includes mixing the first plastic resin with the second plastic resin and extruding the resin mixture such that said medical grade amide compound is present on an inner surface of said medical tube after extrusion to promote release of contacting surfaces of said inner surface of the medical tubing after contact.

9 Claims, 5 Drawing Sheets

U.S. PATENT DOCUMENTS

| | | | |
|---|---|---|---|
| 2006/0235118 A1* | 10/2006 | Selby et al. | 524/186 |
| 2008/0215016 A1 | 9/2008 | Igarashi et al. | |
| 2009/0250137 A1* | 10/2009 | Ruskin | 138/146 |
| 2010/0010175 A1* | 1/2010 | Coffy et al. | 526/86 |
| 2010/0152383 A1* | 6/2010 | Jiang et al. | 525/53 |
| 2011/0026889 A1* | 2/2011 | Risch et al. | 385/102 |
| 2011/0061162 A1* | 3/2011 | Judge | 5/81.1 R |

* cited by examiner

NON-STICK MEDICAL TUBING

FIELD OF THE INVENTION

The invention relates generally to medical equipment. More particularly, the invention relates to medical tubing.

BACKGROUND OF THE INVENTION

Many times, medical tubing is clamped long and short term with devices such as hemostats, roller clamps and pinch clamps. One problem with clamping is that after the clamp is removed from the tubing, the inner walls of the tubing become stuck together and the opening is partially or fully occluded. The occluded line restricts or stops flow of fluids to the patient.

The appearance of tube occlusion makes clinicians pinch tubing and massage the kink out and when tubing still looks occluded, clinicians discard the existing tubing and start a new one. If the restriction is not identified, line occlusion could lead to improper administration of fluids to a patient. The sticking of tubing after clamping ultimately results in lost time, increased costs and possible patient harm.

SUMMARY OF THE INVENTION

Embodiments of the present invention include a method for manufacturing a non stick medical tube. The method includes providing a first plastic resin to a tubing extrusion device and providing a second plastic resin to a tubing extrusion device, the second plastic resin comprising a medical grade amide compound. The method further includes mixing the first plastic resin with the second plastic resin and extruding the resin mixture such that the medical grade amide compound is present on an inner surface of the medical tube after extrusion to promote release of contacting surfaces of the inner surface of the medical tubing after contact.

Embodiments of the present invention also include a non-stick medical tubing. The medical tubing includes a plastic resin mixture including a first plastic resin component and a second plastic resin component, the second plastic resin comprising a medical grade amide compound. The plastic resin mixture is extruded by an extruding apparatus such that the medical grade amide compound is present on an inner surface of the medical tube after extrusion to promote release of contacting surfaces of the inner surface of the medical tubing after contact.

BRIEF DESCRIPTION OF THE DRAWINGS

The features, objects and advantages of the present invention will become more apparent from the detailed description set forth below when taken in conjunction with the drawings in which like references identify correspondingly throughout, and wherein.

DETAILED DESCRIPTION OF EMBODIMENTS

Certain embodiments of the invention will now be described in detail with reference to the figures.

Figure 1:
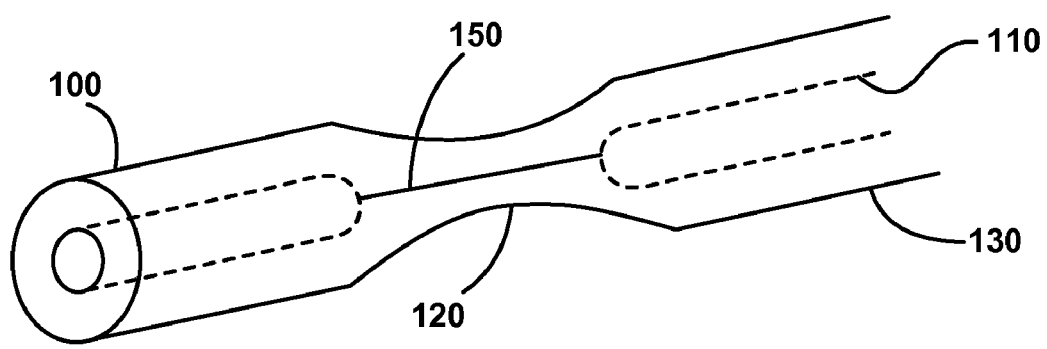
FIG. 1 shows a prior art medical tube with occlusion after to a clamping force has been applied.

FIG. 1 shows a conventional prior art medical tube 100 having an outer surface 130 and an inner surface 110. After a clamping force 120 is applied to the tubing, the inner surfaces 110 of the tube 100 contact each other and become stuck together at occlusion 150.

The occlusion 150 can damage the tubing, requiring replacement and can also cause possible patient harm. Ultimately, time is lost, cost increase and patient safety is at risk with conventional medical tubing that can kink or stick together.

Embodiments of the present invention include a medical tube comprising a medical grade amide compound that is added to the material prior to or during extrusion to prevent lumen sticking and immediately opens up after a clamping force is applied to the tube. Embodiments of the present invention are well suited for preventing lumen occlusion after both short term and long term clamping. For example, embodiments of the present invention can prevent line sticking after a clamping force has been applied to a line for as long as 14 days. The non stick medical tubing of the present invention is also well suited to be used as the pumping section of a peristaltic pump.

The tubing of the present invention is made in part from an amide compound that prevents sticking of the inner surfaces of the tube after they contact each other from clamping or kinking. Embodiments of the present invention are well suited to prevent line sticking after clamping for up to 14 days.

Figure 2:
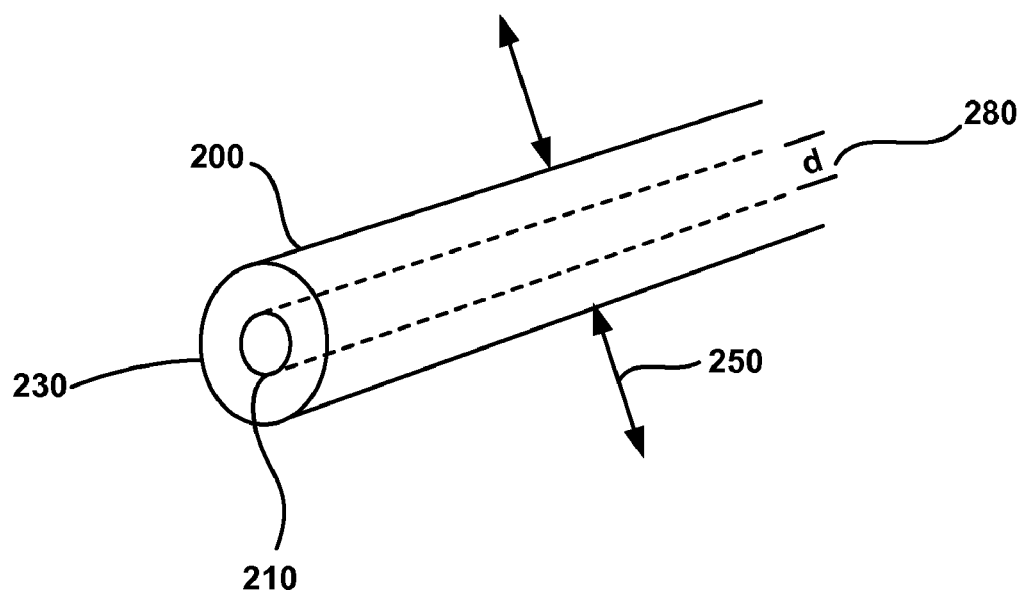
FIG. 2 shows an exemplary non-stick medical tube comprising a medical grade amide compound for preventing occlusion after a clamping force has been applied to the tube in accordance with embodiments of the present invention.

FIG. 2 shows an exemplary non-stick medical tube 200 comprising a medical grade amide compound for preventing occlusion after a clamping force 250 has been applied to the tube in accordance with embodiments of the present invention.

The amide compound serves as a release agent that promotes release of contacting surfaces in the tube. For example, when clamping a tube, the opposing surfaces of the inner passageway contact each other and form an occlusion that blocks or reduces flow. With the non-stick medical tubing of the present invention, after the clamp is released, the contacting surfaces release and the occlusion frees and the tubing is restored to the original shape and function.

As opposed to the prior art medical tubing 100 of FIG. 1, the tubing of the present invention 200 does not stick and form an occlusion in the tube after the clamping force 250 is removed from the outer surface 230 of the tube 200. FIG. 2 shows the inner surface 210 of the tube 200 does not stick and the inner diameter 280 of the tubing is restored after the clamping force 250 is removed from the tube.

It is appreciated that although a medical grade amide compound is described as the release agent, other medical agents could be used. For example, any medical grade compound that reduces sticking of the line lumens and that can be integrated into the extrusion process could be used. One such compound is a medical grade wax.

One example of a suitable amide compound that can be used in accordance with the present invention is an amide fatty acid. An amide fatty acid is an unsaturated long chain carboxylic acid amide and can be found in both food and medical grade. One chemical formulation of an amide fatty acid in accordance with the present invention is $C_{22}H_{43}NO$.

Embodiments of the present invention include adding plastic resin containing an amide compound to the plastic resin used in tube extrusion. By mixing the amide compound into the plastic prior to extrusion, the amide compound is present on the inner tube surface and prevents lumen sticking and lumen occlusions.

In one embodiment of the invention, the base material for the tubing is thermoplastic elastomer (TPE) resin. A secondary material comprising an amide compound is added to the TPE prior to the extrusion process to reduce lumen occlusion and kinking. In one embodiment, all materials of the tubing are formed into pellets prior to extrusion. In one embodiment, a single pellet comprises the mixture of primary (TPE) and secondary (amide fatty acid) materials.

Figure 3:
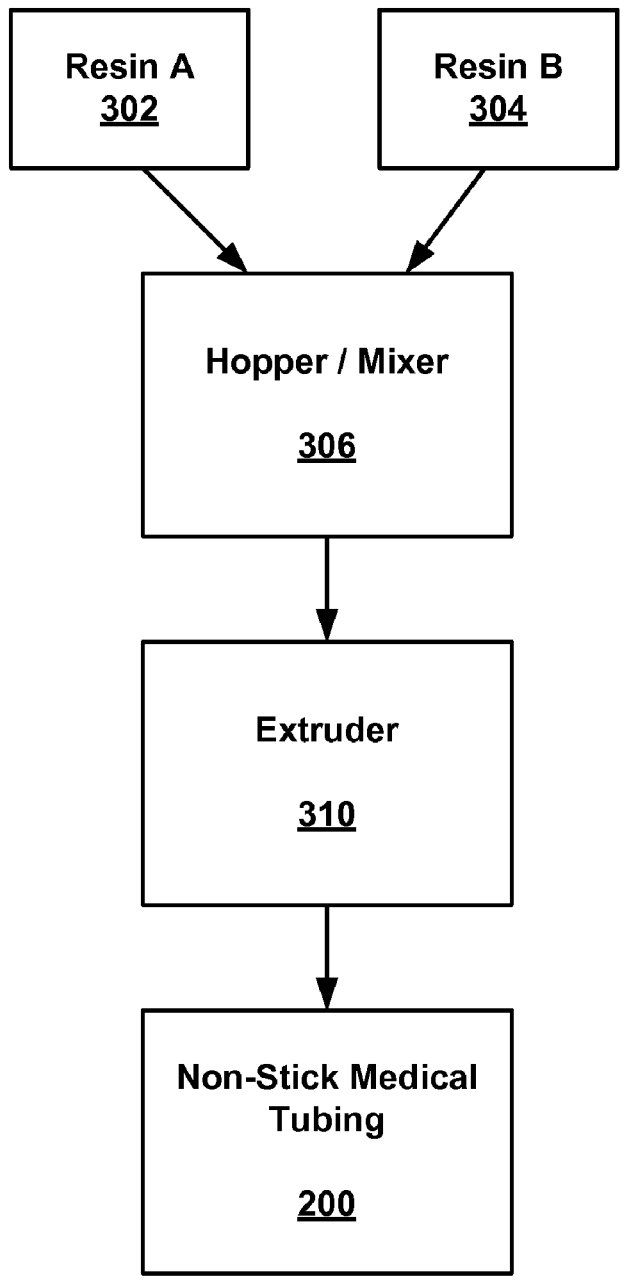
FIG. 3 shows an exemplary system for extruding a non-stick medical tube comprising a medical grade amide compound for preventing occlusion in accordance with embodiments of the present invention.

FIG. 3 shows an exemplary system 300 for extruding a non-stick medical tube comprising a medical grade amide compound for preventing occlusion in accordance with embodiments of the present invention.

Resin A 302 and resin B 304 enter a hopper/mixer 306. In one embodiment, resin A 302 is a thermoplastic elastomer (TPE) resin. In another embodiment, resin A is a polyvinylchloride (PVC), polyurethane or any other plastic resin. In one embodiment of the invention, the resin is delivered to hopper/mixer 306 in pellet form. In one embodiment, resin A and resin B are both part of a homogeneous pellet mixture where a single pellet comprises both resin A 302 and resin B 304.

Resin B 304 included an amide compound and in one embodiment, a carrier compound. Since the amide compound may have different physical properties from the resin A 302, a carrier compound can be mixed with the amide compound to prevent problems during extrusion. The carrier compound aids in mixing of the amide compound with the TPE or PVC. In one embodiment, the carrier compound includes polypropylene, polyethylene, or any other plastic resin. In one embodiment, a specific ratio of amide compound to carrier compound is used to achieve a predetermined amount of amide compound in the extruded tubing.

In one embodiment, the percentage of weight of the amide compound can be between 0.3% and 5% of the tube material after extrusion. In one embodiment, the percentage of weight of the amide compound can be between 1% and 25% of resin B 304.

Resin A 302 and resin B 304 are mixed in hopper 306. The amount of resin A 302 and resin B 304 that enter the hopper/mixer 306 is determined based on the final desired concentration of the amide compound in the tubing. The final concentration depends on the starting concentration of the amide compound in resin B 304 as well as other factors. In one embodiment, a mixture of resin A and resin B is provided in a single pellet whereby the hopper 306 receives a homogeneous mixture of pellets that have both resin A and resin B in them. The ratio of resin A to resin B can be modified to achieve different tube characteristics.

Once the desired mixture of resin A 302 and resin B 304 is determined and provided to hopper/mixer 306, the mixture of resin A 302 and resin B 304 enters the extruder 310. In one embodiment, altering configuration of the extruder 310 can modify the final concentration of the amide compound in the tubing.

For example, altering the extrusion process can modify the concentration of amide compound in the extruded tube. Some processes may facilitate heavier concentration of the amide at different locations of the tube. For example, localized heating during the extrusion process can form higher concentrations of the amide compound on the inner walls of the tube compared to the outer surface of the tube.

The non-stick medical tubing 200 of the present invention exits the extruder. In one embodiment, subsequent operations may be performed on the tubing to facilitate blooming of amide compound to the inner tube walls. Sterilization may also be performed after extrusion.

The non-stick tubing of the present invention does not stick and immediately opens up for fluid flow after short term and long term clamping. One example of short term clamping is the action of a peristaltic pump. In a peristaltic pump, a line segment (tube) is squeezed in a linear motion to create a pumping force. The squeezing can cause lumen sticking. The non-stick medical tubing 200 of the present invention is well suited to be used as the pump segment in a peristaltic pump.

Figure 4:
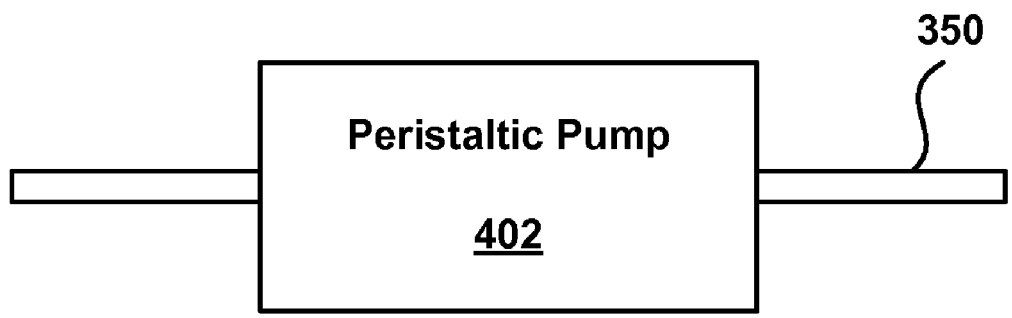
FIG. 4 shows an exemplary peristaltic pump with a non-stick medical tube comprising a medical grade amide compound for preventing occlusion in accordance with embodiments of the present invention.

FIG. 4 shows an exemplary peristaltic pump 402 with a non-stick medical tube 200 comprising a medical grade amide compound for preventing occlusion in accordance with embodiments of the present invention. In conventional peristaltic pumps, a separate pump line segment is used to prevent line occlusion. With the non-stick medical tubing of the present invention, a separate line segment is not needed and the non-stick medical tube of the present invention can be used as the pumping segment.

Figure 5:
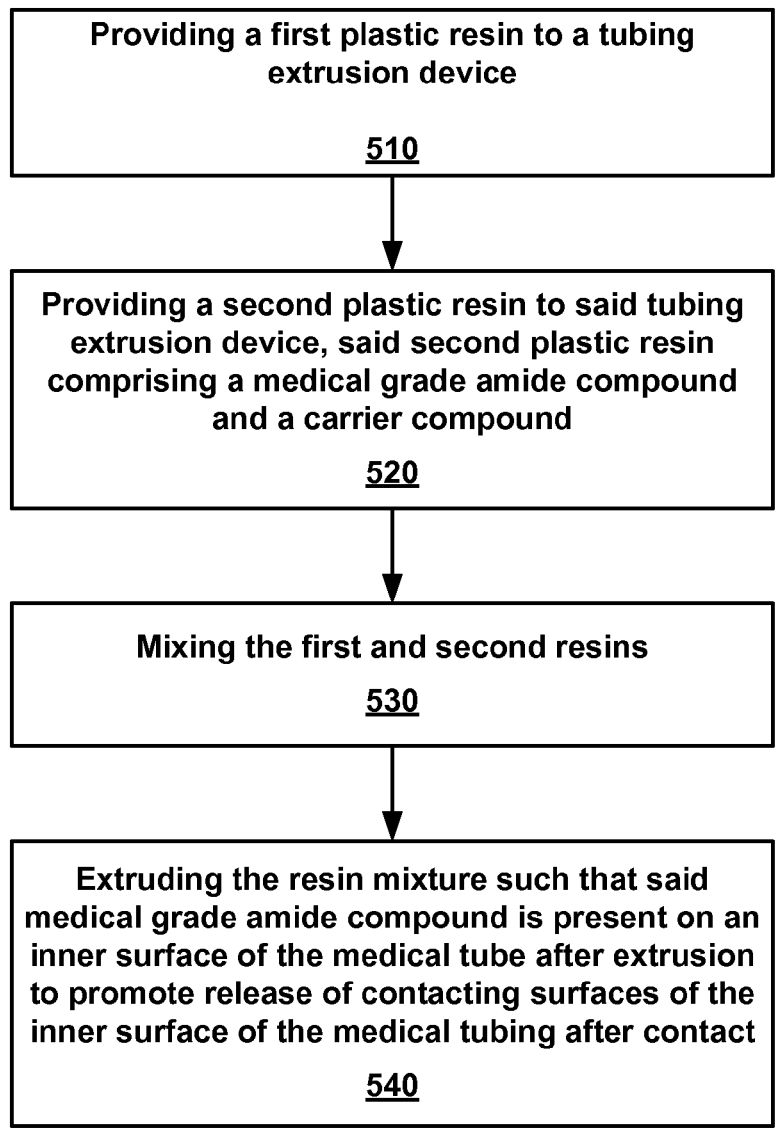
FIG. 5 is a flow diagram of an exemplary method for manufacturing a non-stick medical tube comprising a medical grade amide compound in accordance with embodiments of the present invention.

FIG. 5 is a flow diagram of an exemplary method 500 for manufacturing a non-stick medical tube comprising a medical grade amide compound in accordance with embodiments of the present invention.

At 502, method 500 includes providing a first plastic resin to a tubing extrusion device. In one embodiment, the first resin includes a TPE resin or a PVC resin.

At 504, method 500 includes providing a second plastic resin to the tubing extrusion device, the second plastic resin comprising a medical grade amide compound and in one embodiment, a carrier compound. In one embodiment, the carrier compound includes polypropylene, polyethylene, or any other plastic resin. In one embodiment, the percentage of weight of the amide compound can be between 1% and 25% of the second resin.

At 530, method 500 includes mixing the first plastic resin with the second plastic resin. In one embodiment, the percentage of weight of the amide compound can be between 0.1% and 5% of the mixture. In one embodiment, the first and second plastic resins are mixed and formed into pellet form so that both the first and second plastics are in a single pellet.

At 540, method 500 includes extruding the resin mixture such that the medical grade amide compound is present on an inner surface of the medical tube after extrusion to promote release of contacting surfaces of the inner surface of the medical tubing after contact.

Conclusion

Thus, those of skill in the art will appreciate that the non-stick medical tube of the present invention reduces lumen occlusion, improves patient safety and reduces costs.

One skilled in the art will appreciate that the non-stick medical tubing may be adapted to carry out the objects and obtain the ends and advantages mentioned, as well as those inherent therein. The methods, procedures, and devices described herein are presently representative of embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as disclosed herein.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the disclosure.

What is claimed is:

1. A method for manufacturing a non stick medical tube comprising:
    providing a first plastic resin to a tubing extrusion device;
    providing a second plastic resin to said tubing extrusion device, said second plastic resin comprising a medical grade amide compound;
    mixing said first plastic resin with said second plastic resin;
    extruding the resin mixture as a mono-layered tube such that said medical grade amide compound is present on an inner surface of said medical tube after extrusion to promote release of contacting surfaces of said inner surface of said medical tubing after contact; and
    heating a portion of said mono-layered tube to facilitate migration of said medical grade amide compound to an inner portion of said medical tubing such that more of said medical grade amide compound is located on the inner surface of the tubing than an outer surface of the mono-layered tube.

2. The method of claim 1 wherein said mixing is configured such that said medical grade amide compound is between 0.3% and 5% of said medical tubing.

3. The method of claim 1 wherein said first plastic resin is a thermoplastic elastomer resin.

4. The method of claim 1 wherein said first plastic resin is a Poly Vinyl Chloride (PVC) resin.

5. The method of claim 1 wherein said medical grade amide compound comprises an amide fatty acid.

6. The method of claim 1 wherein said medical grade amide compound comprises medical grade wax.

7. The method of claim 1 wherein said first plastic resin comprises polypropylene.

8. The method of claim 1 wherein said first plastic resin comprises polyethylene.

9. The method of claim 1 wherein said medical grade amide compound comprises between 10% and 25% of said second plastic resin.

* * * * *